(12) United States Patent
Schmidt et al.

(10) Patent No.: US 6,476,275 B2
(45) Date of Patent: Nov. 5, 2002

(54) PROCESS FOR THE CATALYTIC SELECTIVE OXIDATION OF A HYDROCARBON COMPOUND IN PRESENCE OF MESOPOROUS ZEOLITE

(75) Inventors: Iver Schmidt, Copenhagen (DK); Michael Brorson, Charlottenlund (DK); Claus J. H. Jacobsen, Jægerpris (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 09/961,019

(22) Filed: Sep. 21, 2001

(65) Prior Publication Data

US 2002/0038057 A1 Mar. 28, 2002

(30) Foreign Application Priority Data

Sep. 25, 2000 (DK) .......................................... 2000 01410

(51) Int. Cl.$^7$ .......................... C07C 45/34; C07D 301/12
(52) U.S. Cl. .......................... 568/385; 568/836; 549/531
(58) Field of Search ................................ 549/531, 518; 568/771, 719, 741, 780, 803, 836, 338, 385

(56) References Cited

U.S. PATENT DOCUMENTS

| | | | |
|---|---|---|---|
| 4,410,501 A | 10/1983 | Taramasso et al. | 423/326 |
| 4,824,976 A | 4/1989 | Clerici et al. | 549/531 |
| 5,811,599 A | 9/1998 | Alive et al. | 568/771 |
| 5,874,596 A | 2/1999 | Onozawa et al. | 549/531 |
| 6,037,484 A | 3/2000 | Grey | 549/531 |
| 6,054,112 A | 4/2000 | Hasenzahl et al. | 423/705 |
| 6,106,803 A | 8/2000 | Hasenzahl et al. | 423/705 |
| 6,160,138 A | 12/2000 | Escrig et al. | 549/531 |

FOREIGN PATENT DOCUMENTS

| | | |
|---|---|---|
| EP | 0894783 A1 | 2/1999 |
| WO | 9629297 | 9/1996 |
| WO | WO 98/00415 | 1/1998 |
| WO | WO 01/72636 A1 | 10/2001 |

OTHER PUBLICATIONS

M.G. Clerici, "Catalytic oxidation with hydrogen peroxide: new and selective catalysts," *Studies in Surface Science and Catalysis, Heterogeneous Catalysis and Fine Chemicals III*, vol. 78, *Proceedings of the 3$^{rd}$ International Symposium*, Pointers, France, Apr. 5–8, 1993, pp. 21–33.

A.J.H.P. van der Pol, et al., "Parameters affecting the synthesis of titanium silicalite 1," *Applied Catalysis A: General* (1992) pp. 93–111.

A.J.H.P. van der Pol, et al., "Why are some titanium silicalite–1 samples active and others not?" *Applied Catalysis A: General* (1992) pp. 113–130.

Claus Madsen, et al. ,"Nanosized zeolite crystals–convenient control of crystal size distribution by confined space Synthesis," *Chem. Commun.* (1999), pp. 673–674.

M.C. Capel–Sanchez, et al., "Effective alkene epoxidation with dilute hydrogen peroxide on amorphous silica–supported titanium catalysts," *Chem. Commun.* (2000), pp. 855–856.

J.S. Beck, et al., "A New Family of Mesoporous Molecular Sieves Prepared with Liquid Crystal Templates," Reprinted from *Journal of the American Chemical Society* (1992), vol. 114, pp. 10834–10843.

A. Carati, et al., "Stability of Ti in MFI and Beta structures: a comparative study," *Microporous and Mesoporous Materials*, vol. 30 (1999), pp. 137–144.

Claus J.H. Jacobsen, et al., "Mesoporous Zeolite Single Crystals," Reprinted from *Journal of the American Chemical Society*, vol. 122, No. 29, pp. 7116–7117 (2000).

Iver Schmidt, et al., "Confined Space Synthesis. A Novel Route to Nanosized Zeolites," Reprinted from *Inorganic Chemistry*, vol. 39, No. 11, pp. 2279–2283 (2000).

*Primary Examiner*—Sreeni Padmanabhan
(74) *Attorney, Agent, or Firm*—Dickstein Shapiro Morin & Oshinsky, LLP

(57) ABSTRACT

Processes applying mesoporous titanium containing zeolite based catalysts for selective oxidation or epoxidation of hydrocarbons by peroxides.

14 Claims, 1 Drawing Sheet

○  Epoxidation of Cyclohexene
□  Epoxidation of 1-octene

PROCESS FOR THE CATALYTIC SELECTIVE OXIDATION OF A HYDROCARBON COMPOUND IN PRESENCE OF MESOPOROUS ZEOLITE

The present invention is directed to selective oxidation of hydrocarbons with hydrogen peroxide by contact with mesoporous titanium-containing zeolite catalyst.

The catalytic properties of titanium silicalite-1 (TS-1) for selective oxidation and epoxidation of various organic compounds with aqueous hydrogen peroxide are described in U.S. Pat. No. 4,410,501. However, TS-1 suffers from intracrystalline diffusion limitations due to the small size of the zeolite micropores. This limitation is most pronounced for low temperature, liquid-phase reactions with bulky reactants and products. This has stimulated research into zeolites with larger pores (e.g. BEA, UTD-1) and amorphous, mesoporous, titanium-containing materials.

U.S. Pat. No. 5,811,599, which is incorporated herein by reference, discloses a process for the oxidation of hydrocarbons with hydrogen peroxide ($H_2O_2$) using an amorphous titanium-silicate catalyst. This catalyst is suitable for oxidation and hydroxylation of different organic substrates of various molecular sizes. However, its amorphous state makes it difficult to handle in practice, and therefore simple processes such as filtration present practical problems.

Mesoporous materials only exhibit high selectivity towards epoxides if organic peroxides are used as oxidants. This reduces the environmental and economic advantages, since management of by-products due to reduced selectivity and decomposition of the organic oxidant becomes an important issue. Comparative studies of TS-1 and Ti-BEA have shown that different catalytic behaviour and lifetime are to be expected, i.e. the excellent catalytic properties of TS-1 might not be observed for Ti-BEA (A. Carati, C. Flego, E. Provide Massara, R. Millini, L. Carluccio, W. O. Parker Jr., G. Bellussi, Microporous Mesporous Mat, 1999, 30, 137). The diffusion properties of TS-1 catalysts can be altered by preparation of nano-sized TS-1, but separation of the finely crystalline catalyst from the product mixture involves costly high-speed centrifugation or flash distillation.

WO Patent Application No. 96/29297, incorporated herein by reference, discloses a method for catalytic peroxide oxidation or hydroxylation reaction of large organic molecules, utilising mesoporous, silicate molecular sieves based on templating agents of neutral amines, diamines or quarternary ammonium salts. MCM-41 types of molecular sieves are formed. These materials have a micellar structure, and their X-Ray diffraction patterns do not reveal any reflections at $2\theta$ angles above 8 degrees, indicating that they are not crystalline zeolites.

U.S. Pat. No. 5,974,596, which is incorporated herein by reference, discloses a titanosilicate catalyst with mesopores for oxidation of organic compounds. This catalyst comprises spherical, crystalline, primary particles combined with one another to form secondary particles, the combined part of the primary particle being the crystalline substance. The mesopores consist of the intercrystalline pores formed between the primary particles. This agglomeration of primary particles to form secondary particles and thus the catalyst is obtained by decreasing the pH of a slurry of primary particles.

Recently, preparation of mesoporous zeolite single crystals has been described in Danish Patent Application No. PA1999 01745. Compared to conventional zeolite crystals, those mesoporous crystals exhibit significantly improved diffusion properties (C. J. H. Jacobsen, J. Houszvicka, I. Schmidt, A. Carlsson, J.Am.Chem.Soc, 2000, 122, 7116).

There is therefore the need for hydrocarbon oxidation and hydroxylation processes using crystalline, zeolite catalysts effective in selective oxidation of hydrocarbons.

It has now been found that crystalline, titanium-containing zeolites with a mesoporous structure have improved catalytic activity in the selective oxidation of hydrocarbon compounds and epoxidation of alkenes with peroxides. In particular, mesoporous TS-1 catalyst is shown to be active in epoxidation of 1-octene and significantly more active in epoxidation of cyclohexene than conventional TS-1.

This invention describes a process for selective oxidation or epoxidation of hydrocarbon compounds and functionalised hydrocarbons by reaction with hydrogen peroxide in presence of a crystalline, mesoporous titanium-containing zeolite.

Accordingly, the invention concerns a process for the selective oxidation of a hydrocarbon compound by reaction with peroxide in the presence of a crystalline, mesoporous, titanium-containing zeolite catalyst, characterised in that the zeolite catalyst consists of individual, primary crystals having intra-crystalline mesopores obtained by crystallisation of the zeolite in a carbon matrix, the zeolite catalyst having at least one X-Ray Powder Diffraction (XRPD) reflection in the $2\theta$ range 8–30 degrees determined by the zeolite type.

An object of the invention is to provide a hydrocarbon oxidation process using crystalline, mesoporous titanium-containing zeolite catalysts.

Another object of the invention is to provide a hydrocarbon oxidation process using crystalline, mesoporous titanium-containing zeolite catalysts having improved thermal and hydrothermal stability.

Yet another object of the invention is to provide a hydrocarbon oxidation process using a zeolite catalyst consisting of individual, primary crystals having intracrystalline mesopores obtained by crystallisation of the zeolite in a carbon matrix.

A further object of the invention is to provide a hydrocarbon oxidation process using a crystalline, mesoporous titanium-containing zeolite catalyst having at least one X-Ray Powder Diffraction (XRPD) reflection in the $2\theta$ range 8–30 degrees determined by the zeolite type.

Functionalised hydrocarbons are hydrocarbon compounds containing groups or atoms being able to react with oxygen, such as organic sulphur and nitrogen compounds, alcohols, olefins and aromatic and aliphatic C-H bonds as further mentioned by M. G. Clerici, in "Heterogeneous Catalysis and Fine Chemicals III", page 21, M. Guisnet et al. (Eds.), Elsevier, 1993.

The mesoporous zeolites applied in the process of the invention are prepared by crystallisation in a mesoporous, carbon matrix followed by removal of the matrix by combustion, selective dissolution or evaporation. The mesopores in the titanium-containing zeolites result from the removal of the matrix. The mesopores are situated in close to 100% of the individual zeolite crystals and the mesopore volume is above 0.2 ml/g of titanium-containing zeolite.

The invention will be apparent in more detail by the following description and examples.

The terms "mesoporous" or "mesopore" as used herein refers to mesoporous zeolites containing pores within each crystal having a pore-size range according to the IUPAC definition of mesopores of 2 nm<pore diameter<50 nm. Contrary to nanosized TS-1, separation of mesoporous TS-1 from the product mixture requires solely simple filtration.

EXAMPLES

Mesoporous TS-1 was prepared as follows: Carbon Black Pearls 700® (supplied by Carbot Corp.) with an average particle diameter of 18 nm (ASTM D-3249) is impregnated to incipient wetness with a clear solution of tetrapropylammonium (TPA) hydroxide, water and ethanol. After evaporation of the ethanol component of the mixture, the carbon particles are impregnated with 20% excess (relative to incipient wetness) of a mixture of tetraethylorthotitanate and tetraethylorthosilicate. The composition of the resulting synthesis gel is:

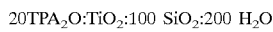

20TPA$_2$O:TiO$_2$:100 SiO$_2$:200 H$_2$O and the resulting zeolite concentration is approximately 20 wt %. After ageing for a minimum of 3 hours at room temperature, the impregnated carbon black was introduced into a stainless steel autoclave containing sufficient water to produce saturated steam.

The autoclave was heated slowly (0.5° C./min) to 170° C. and kept there for 72 hours. After cooling the autoclave to room temperature, the product was suspended in water and isolated by suction filtration. The product is washed four times by suspension in water and then dried at 110° C. for 10 hours. The carbon black was removed in a muffle furnace by controlled combustion in air at 550° C. for 8 hours. In this way a white material is obtained, which by chemical analysis is shown to contain less than 0.5 wt %. Conventional, micron-sized TS-1 with similar titanium content was used as a reference.

X-Ray Powder Diffraction, XRPD, showed that both samples consisted of highly crystalline MFI-structured material, which is well known to have reflection angles in the range 8–30 degrees for a zeolite material. Characterisation by diffuse UV-vis Reflectance Spectroscopy and Raman Spectroscopy verified the presence of titanium in the zeolite framework, and no extra framework anatase was detected. Chemical analysis of the two TS-1 samples gave Si/Ti ratios of 110 in both cases. Scanning Electron Microscopy of the reference TS-1 revealed a highly crystalline material consisting of twinned coffin-shaped crystals with a narrow size distribution around approximately 1.5 μm.

Relatively large (approximately 0.3–1.2 μm) and well-shaped, single crystals are obtained by hydrothermal crystallisation in carbon black. Inspection of high resolution transmission electron micrographs revealed lattice fringes extending through the entire crystal. The significant mesoporosity was observed as bright spots, approximately 20 nm in diameter dispersed throughout the entire crystal.

This diameter matches that of the diameter of the carbon primary particles (18 nm) that occupy these positions prior to combustion. It was shown by N$_2$ adsorption/desorption that the mesoporous TS-1 exhibited a porosity similar to that reported previously for ZSM-5 prepared by a similar route (micropore volume 0.09 ml/g and mesopore volume 1.01 ml/g determined by t-plot method and BJH desorption, respectively).

Catalytic test:

The two TS-1 samples were tested as catalysts for epoxidation of 1-octene and cyclohexene with aqueous hydrogen peroxide using methanol as solvent and n-heptane as internal standard. The reaction was performed at ambient pressure in a magnetically stirred round-bottomed flask fitted with a condenser and placed in a thermostat oil bath. Alkene (4.2 ml of 1-octene or 2.7 ml of cyclohexene), 20.0 ml methanol, 0.75 ml n-heptane (internal standard) and 0.18 g of TS-1 catalyst were added to the flask and preheated to reaction temperature (40° C.).

Figure 1:
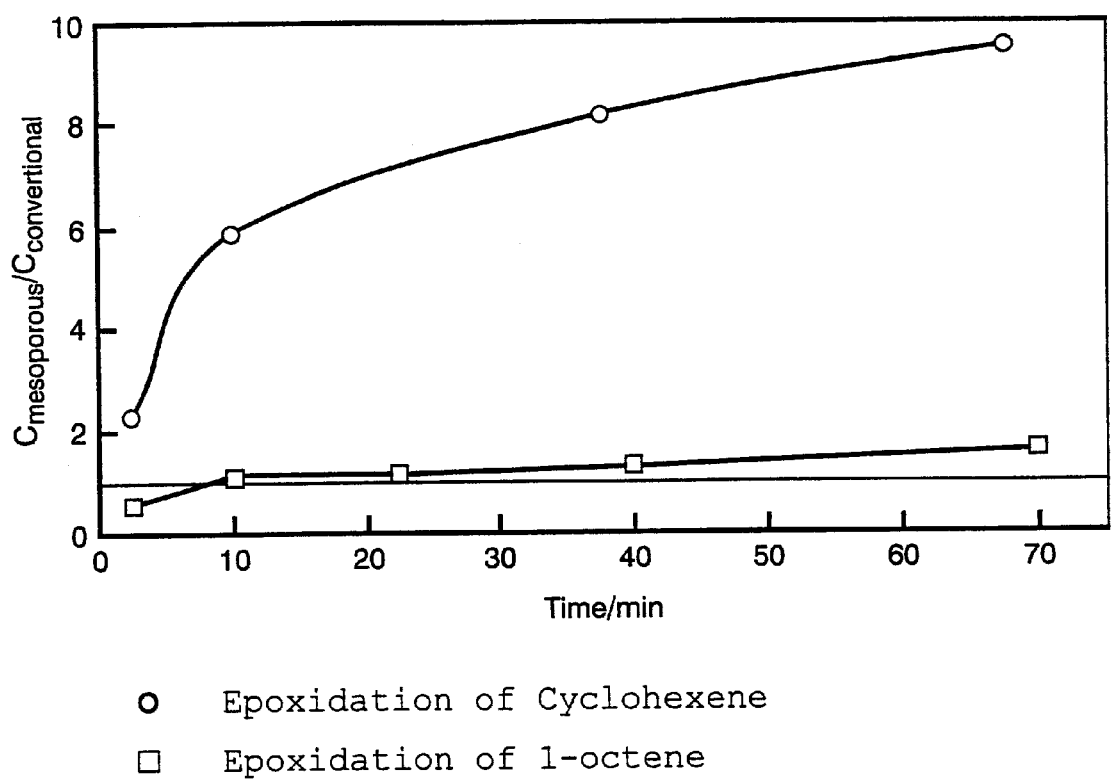
FIG. 1 compares the epoxidation of cyclohexene and 1-octene.

The kinetic experiment was started when 0.50 ml 35 wt % H$_2$O$_2$ was added. Samples of the reaction mixture were taken at regular intervals. The zeolite catalyst removed by filtration and analysed by Gas Chromatography, GC, cooled the samples. The initial hydrogen peroxide to olefin molar ratio was 0.25 and the molar ratio of H$_2$O$_2$ to titanium was approximately 230. Selectivity towards corresponding epoxides was more than 90% in all tests. Plotting the ratio of product concentrations as a function of time compares the catalytic performance of the two types of TS-1. This is illustrated in FIG. 1 of the attached drawing for the epoxidation of 1-octene and cyclohexene.

Similar product concentrations ($C_{mesoporous}/C_{conventional}=$ 1) are obtained when epoxidation of 1-octene is catalysed by mesoporous and by conventional TS-1. Thus, epoxidation of 1-octene is not limited by intra-crystalline diffusion and therefore not dependent on the zeolite crystal size. The results also show that the intrinsic activity of mesoporous TS-1 is similar to conventional TS-1. In contrast, the epoxidation of cyclohexene exhibits a product concentration ratio, which exceeds a value of 10 within the contact times used in the experiments.

Since the experiments with 1-octene suggest similar intrinsic activity of the two types of TS-1, the enhanced catalytic performance of the mesoporous sample must be due to a better accessibility of the active sites. Thus, the improved catalytic activity of the mesoporous TS-1 is attributed to its improved diffusion properties compared with conventional micron-sized TS-1. Compared with conventional TS-1, mesoporous TS-1 improves the catalytic performance without changing the product distribution, which might be an advantage compared with the alternative of using titanium-containing zeolltes with larger pores.

What is claimed is:

1. Process for the selective oxidation of a hydrocarbon compound by reaction with peroxide in the presence of a crystalline, mesoporous, titanium-containing zeolite catalyst, characterised in that the zeolite catalyst consists of individual, primary crystals having intra-crystalline mesopores obtained by crystallisation of the zeolite in a carbon matrix, the zeolite catalyst having at least one X-Ray Powder Diffraction (XRPD) reflection in the 2θ range 8–30 degrees determined by the zeolite type.

2. Process for the selective oxidation of an organic compound by reaction with peroxide in the presence of a crystalline, mesoporous, titanium-containing zeolite catalyst, characterized in that the zeolite catalyst consists of individual, primary crystals having intra-crystalline mesopores obtained by crystallization of the zeolite in a carbon matrix, the zeolite catalyst having at least one X-Ray Powder Diffraction (XRPD) reflection in the 2θ range 8–30 degrees determined by the zeolite type, the organic compound being selected from the group consisting of sulfur compounds, nitrogen compounds, alcohols, olefins, aliphatic hydrocarbons and aromatic hydrocarbons.

3. Process of claim 1, wherein the hydrocarbon compound is an alkene epoxidised by reaction with peroxide in presence of the mesoporous, titanium-containing zeolite catalyst.

4. Process of claim 2, wherein the organic compound comprises alkanes and alcohols being oxidised selectively to alcohols and aldehydes or ketones by reaction with peroxide in presence of the mesoporous, titanium-containing zeolite catalyst.

5. Processes of claim 1, wherein the crystalline, mesoporous titanium-containing zeolite catalyst is prepared by crystallisation in a mesoporous, carbon matrix followed by removal of the matrix by combustion, selective dissolution and/or evaporation.

6. Process of claim 5, wherein the matrix consists of carbon.

7. Processes of claim 1, wherein the peroxide is selected from aqueous hydrogen peroxide and/or organic peroxides.

8. Process according to claim 1, wherein the mesoporous volume of the titanium-containing zeolite is at least 0.2 ml/g.

9. Process for the selective oxidation of an organic compound by reaction with peroxide in the presence of a crystalline, mesoporous, titanium-containing zeolite catalyst, characterized in that the zeolite catalyst consists of individual, primary crystals having intra-crystalline mesopores obtained by crystallization of the zeolite in a carbon matrix, the zeolite catalyst having at least one X-Ray Powder Diffraction (XRPD) reflection in the 2θ range 8–30 degrees determined by the zeolite type, the organic compound being selected from the group consisting of sulfur compounds, nitrogen compounds, alcohols, olefins, aliphatic hydrocarbons and aromatic hydrocarbons, wherein the mesoporous volume of the titanium-containing zeolite is at least 0.2 ml/g.

10. Process according to claim 3, wherein the mesoporous volume of the titanium-containing zeolite is at least 0.2 ml/g.

11. Process according to claim 4, wherein the mesoporous volume of the titanium-containing zeolite is at least 0.2 ml/g.

12. Process according to claim 5, wherein the mesoporous volume of the titanium-containing zeolite is at least 0.2 ml/g.

13. Process according to claim 6, wherein the mesoporous volume of the titanium-containing zeolite is at least 0.2 ml/g.

14. Process according to claim 7, wherein the mesoporous volume of the titanium-containing zeolite is at least 0.2 ml/g.

* * * * *